United States Patent [19]
Pietilä et al.

[11] Patent Number: 6,112,603
[45] Date of Patent: Sep. 5, 2000

[54] METHOD AND A DEVICE FOR HANDLING SAMPLE PLATES

[75] Inventors: Pekka Pietilä, Turku; Petri Kivelä, Piispanristi, both of Finland

[73] Assignee: Wallac Oy, Turku, Finland

[21] Appl. No.: 09/210,570

[22] Filed: Dec. 14, 1998

[30] Foreign Application Priority Data

Dec. 15, 1997 [FI] Finland ..................... 974521
Dec. 7, 1998 [FI] Finland ..................... 982645

[51] Int. Cl.⁷ ............................... G01N 1/00
[52] U.S. Cl. ............................... 73/863.23
[58] Field of Search ..................... 73/863, 863.23, 73/864.21, 864.22, 864.23; 422/63, 64; 494/10, 33; 366/140, 109, 110, 118, 138

[56] References Cited

U.S. PATENT DOCUMENTS

3,591,862  7/1971  Winston .
4,147,294  4/1979  Davidson et al. .
5,073,578  12/1991  Boodaghains et al. .
5,707,861  1/1998  Sherman et al. .

*Primary Examiner*—Robert Raevis
*Attorney, Agent, or Firm*—Kubovcik & Kubovcik

[57] ABSTRACT

A method for handling a microplate, in which liquid (22) is dosed into a sample well (21) and the liquid is removed and, if necessary, the sample wells are further washed and/or rinsed. According to the invention, the liquid to be dosed is dosed into the sample well (21) of the sample plate (10), after which the sample plate is centrifuged so that the centrifugal force is exerted towards the bottom of the sample well to remove air bubbles, and/or the sample plate is centrifuged so that the centrifugal force is exerted away from the bottom of the sample well to empty the sample plate. The device relating to the invention comprises a dosing device and at least one centrifuge (24). In dosing, a distributing valve (14) and a dosing nozzle (12) are usually needed, and where necessary, a vibrator device (32, 33) to bring the liquid (22) in the sample well (21) of the sample plate (10) into a motion. According to one embodiment, the vibrator device (33) comprises a needle (34) that is dipped into the liquid (22) in the sample well (21) of the sample plate (10), and by means of the vibration of the needle air bubbles can also be removed from the liquid.

15 Claims, 9 Drawing Sheets

METHOD AND A DEVICE FOR HANDLING SAMPLE PLATES

The object of the invention is a method for handling a sample plate, such as a microplate, according to which method liquid is dosed into a sample well of a sample plate for biospecific determination, coating or other purpose, after which the liquid is removed and, if necessary, the sample wells are further washed and/or rinsed.

The biospecific determination of medical samples is generally performed using sample plates, whose sample wells have been coated with a suitable coating agent. The coating can be, for example, a protein with bioactivity, which is used to separate the required biomolecule or biocomplex from the reaction solution containing the sample. The sample plates used at present are so-called microplates, in which a large number of sample wells have been placed in matrix form. The generally used number of wells has been 96 wells, but nowadays microplates that have 384, 864 and 1536 wells are becoming more common. Because the size the microplate is standardised so that its outer dimensions are always the same, the size of the wells naturally decreases as the number of wells increases. Nowadays, small sample wells are considered desirable because only a very small amount of sample solution is required for them.

The smaller size of the sample plate's wells has, however, created major problems in handling the sample plate. For example, in a microplate that has 384 sample wells, the size of sample wells is 4.5 mm×4.5 mm, and in a microplate that has 1536 wells, the cross-sectional area of a well can be as small as 2.3 mm$^2$. Known devices cannot coat sample wells of such small size. Neither is the sample solution dosing equipment or rinsing equipment used at present suitable for sample wells of such small size.

The purpose of the present invention is to create a new method for handling small sample wells. It is characteristic of the method relating to the invention that the sample plate is centrifuged in order to take the dosed liquid to the bottom of the sample wells and to remove air bubbles from the sample wells, and that the sample plate is centrifuged in order to remove the dosed liquid from the sample wells.

According to one advantageous embodiment of the invention, it is characteristic that in order to take the dosed liquid to the bottom of the sample wells, the sample plate is centrifuged with the axis of the centrifuge either horizontal or vertical, and that in order to remove the dosed liquid from the sample wells, the sample plate is centrifuged with the axis of the centrifuge turned to a vertical position.

According to another advantageous embodiment of the invention, it is characteristic that in order to fill the sample wells, the sample plate is placed in the centrifuge so that the sample wells are directed towards the axis of rotation of the centrifuge drum, and the sample plate is centrifuged in order to throw the dosed liquid, by means of centrifugal force, against the bottom and walls of the sample well, and that in order to empty the sample wells, the sample plate is placed in the centrifuge so that the sample wells are directed away from the axis of rotation of the centrifuge drum, and the sample plate is centrifuged in order to remove the dosed liquid, by means of centrifugal force, from the sample well.

According to a third advantageous embodiment of the invention, the sample wells of the sample plate are filled in such a way that the liquid container containing the liquid to be dosed is chosen from two or more liquid containers, the liquid to be dosed is passed to the sample well of the sample plate through a distributing valve and via a dosing nozzle, and the sample plate is centrifuged both in order to take the liquid to the bottom of the sample wells and to remove the liquid from the sample wells.

According to a fourth advantageous embodiment of the invention, compressed air or pressurised gas is fed into two or more liquid containers, the liquid to be dosed is passed from a pressurised liquid container through a distributing valve and via a dosing nozzle to the sample well of the sample plate, and the sample plate is centrifuged both in order to take the liquid to the bottom of the sample wells and to remove the liquid from the sample wells.

According to a fifth advantageous embodiment of the invention, dosing of the liquid into the sample wells of the sample plate is carried out periodically in such a way that the sample plate in the conveyor is stopped for dosing when the sample well is at the dosing nozzle, and the sample plate is centrifuged both in order to take the liquid to the bottom of the sample wells and to remove the liquid from the sample wells.

According to a sixth advantageous embodiment of the invention, the dosing of the liquid into the sample wells of the sample plate is carried out continuously in such a way that the sample plate in the conveyor is also in motion during dosing, and the sample plate is centrifuged both in order to take the liquid to the bottom of the sample wells and to remove the liquid from the sample wells.

According to yet another advantageous embodiment, the sample plate or the liquid in the sample well of the sample plate is brought to a vibratory motion to remove air bubbles or to bring the dosed liquid into contact with the bottom and walls of the sample well by means of vibration, and the sample plate is centrifuged in order to remove the liquid from the sample wells.

The object of the invention is also a device for handling a sample plate, such as a microplate, which device comprises a dosing device for feeding liquid into the sample well of a sample plate for biospecific determination, coating or other purpose, and a device for removing the liquid from the sample well.

It is characteristic of the device relating to the invention that the sample plate handling device comprises a centrifuge for centrifuging the sample plate, a feeding device for feeding the sample plate into the centrifuge, sample plate fixing elements for fixing the sample plate to the centrifuge drum in such a way that the sample wells of the sample plate are directed towards the axis of rotation of the centrifuge drum, and sample plate fixing elements for fixing the sample plate to the centrifuge drum in such a way that the sample wells of the sample plate are directed away from the axis of rotation of the centrifuge drum.

In the centrifuge, the sample plate fastening elements have been arranged in such a way that, when a sample plate is attached to the centrifuge, the sample wells are directed towards the axis of rotation of the centrifuge drum. Correspondingly, the sample plate fastening elements of the centrifuge can also be arranged in such a way that, when a sample plate is fastened to the centrifuge, the sample wells are directed away from the axis of rotation of the centrifuge drum.

According to one advantageous embodiment of the device relating to the invention, the centrifuge comprises a turning element, such as an axle, by means of which the centrifuge can be turned so that the axis of the centrifuge drum is vertical during centrifuging.

According to another advantageous embodiment of the device relating to the invention, the sample plate handling device comprises a sampling plate dosing device, which has two or more liquid containers, from which liquid to be dosed can be dosed through a distributing valve and via a dosing nozzle into the sample well of the sample plate, and a centrifuge for filling and emptying the sample plate.

According to a third advantageous embodiment of the device relating to the invention, the dosing device comprises a compressed air or compressed gas device, such as a pump or a pressure chamber, which has been connected to two or more liquid containers for feeding compressed air or gas into these containers, and that the dosing device comprises a distributing valve and a dosing nozzle, by means of which the liquid to be dosed can be chosen from the liquid container containing it for dosing into the sample well of the sample plate.

According to a fourth advantageous embodiment of the device relating to the invention, the dosing device comprises a vibrator device for bringing the liquid in the sample well of the sample plate to a vibratory motion and pressing it against the bottom and walls of the sample well and/or a vibrator device for removing the liquid from the sample well.

According to a fifth advantageous embodiment of the device relating to the invention, the vibrator device is located in conjunction with the sample plate conveyor belt.

According to a sixth advantageous embodiment of the device relating to the invention, the vibrator device comprises at least one spike or needle, which can be positioned in the liquid in the sample well of the sample plate in order to bring the liquid to a vibratory motion and to remove air bubbles or to bring the liquid into contact with the bottom and walls of the sample well.

The dosing device comprises two or more liquid containers, from where the liquid to be dosed can be dosed through a distributing valve and via a dosing nozzle into the sample well of the sample plate. The dosing device also comprises a compressed air or compressed gas device, such as a pump or a pressure tank, which has been connected to two or more liquid containers to feed compressed air or gas into these containers. The liquid which it is desired to dose through the dosing device's distributing valve and dosing nozzle can be selected for dosing from the liquid container that contains it into the sample well of the sample plate.

The dosing device further comprises a vibrator device for bringing the liquid in the sample well of the sample plate to a vibratory motion and for pressing it against the bottom and walls of the sample well, and/or a vibrator device for removing the liquid from the sample well.

The vibrator device can be located in conjunction with the belt of the sample plate conveyor. According to another embodiment, the vibrator device comprises at least one spike or needle which can be placed in the liquid in the sample well of the sample plate in order to bring the liquid to a vibratory motion and to remove air bubbles or to bring the liquid into contact with the bottom and walls of the sample well.

In the following, the invention is described using examples with reference to the accompanying drawings, in which.

Figure 1:
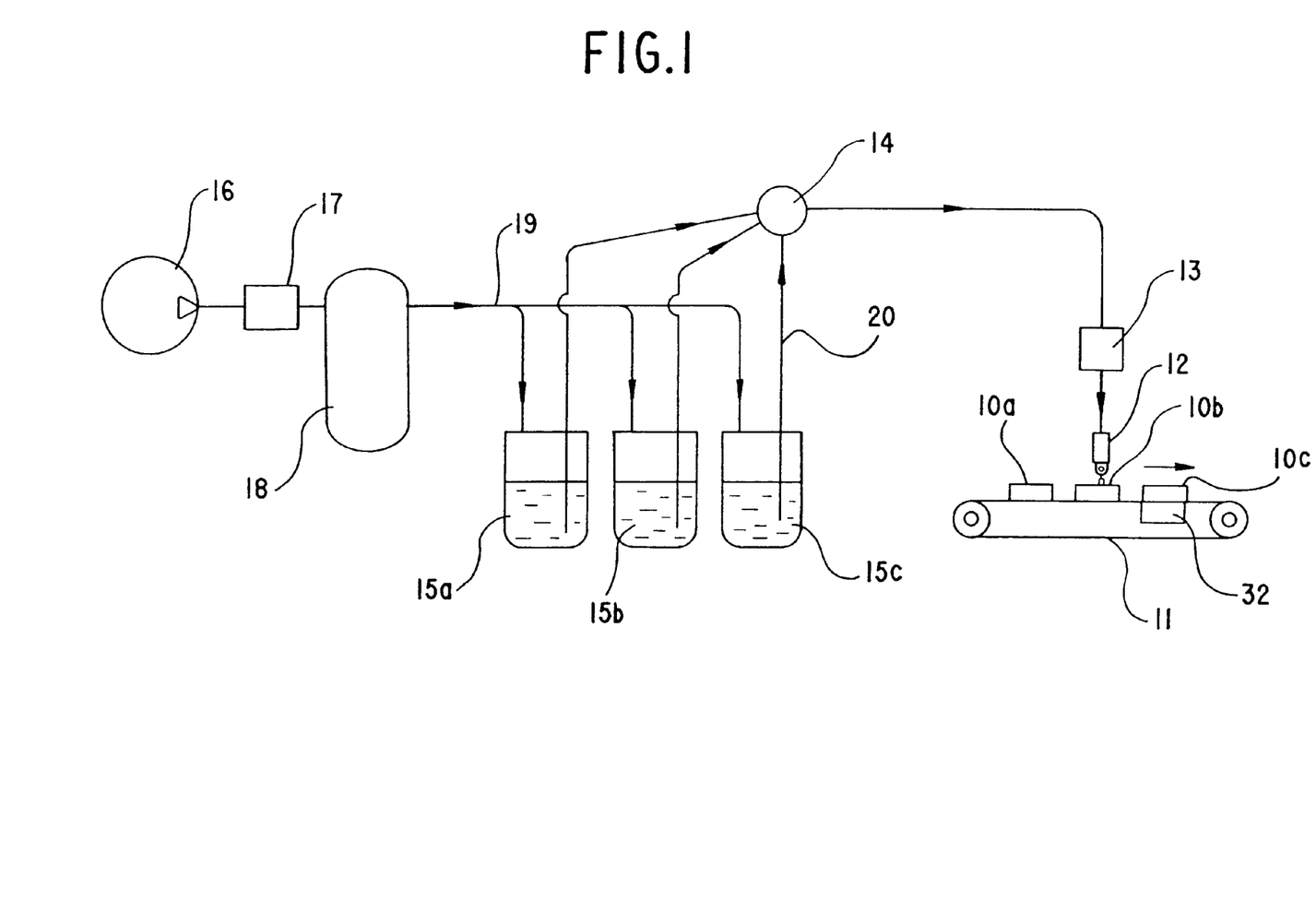
FIG. 1 shows a diagrammatic view of a sample plate dosing device, seen from the side.

FIG. 1 shows equipment for the dosing of sample plates 10, in which the sample plates 10a, 10b and 10c have been placed on a belt conveyor 11. Above the conveyor 11 and the sample plates 10 there is dosing equipment for the liquid to be dosed, which comprises a dosing nozzle 12, a solenoid valve 13, a distributing valve 14 and liquid containers 15a, 15b and 15c. Compressed air is introduced into the liquid containers by means of equipment comprising a compressor 16, a pressure reduction valve 17 and a compressed air tank 18. The compressed air tank 18 is connected via tubes 19 to the liquid containers 15 so that the liquid containers are also at the same pressure as the compressed air tank. By the action of pressure, the liquids in all the liquid containers 15a, 15b and 15c tend to leave the container via the tubes 20. In such case it is possible, using the distributing valve 14, to choose the container 15 from which liquid is taken to the dosing nozzle 12.

In the example described here, the container 15a of the dosing equipment of FIG. 1 contains the liquid used for the coating of the wells of the microplate used as the sample plate. The liquid container 15*b* contains liquid for washing the coating solution and the liquid container 15*c* rinsing liquid. By using this kind of dosing equipment, it is possible to carry out dosing of coating liquid, washing liquid and rinsing liquid into the sample wells of the microplate with the same equipment, without having to carry out the arduous and time-consuming intermediate cleaning procedures required by the known equipment.

In FIG. 1, the sample plates 10 can be moved in relation to the dosing nozzle 12 by means of a conveyor 11, in which case the dosing of the liquid can be carried out into all the sample wells of the microplate 10 one by one. It is also possible to arrange the sample plate to move sideways, but this example only includes the movement in one direction caused by the belt conveyor 11. In such case the dosing can be carried out in one row of sample wells at a time. The dosing nozzle 12 must then have as many nozzle tips as there are sample wells next to each other in one row of the sample plate. The structure of the dosing nozzle is described in more detail in FIG. 3.

In FIG. 1, there is an shaker device 32 in conjunction with the belt conveyor 11, which causes the sample plate 10*c* on the belt to be shaken after the dosing of the liquid. The purpose of the shaker device is to remove air bubbles from the dosed liquid and to ensure that the liquid dosed into the sample well of the sample plate 10 is at the bottom of the well and in contact with the walls of the well. Removal of air bubbles is important, particularly in the dosing of sample well coating liquid, but equally in the dosing of other liquids.

Figure 2:
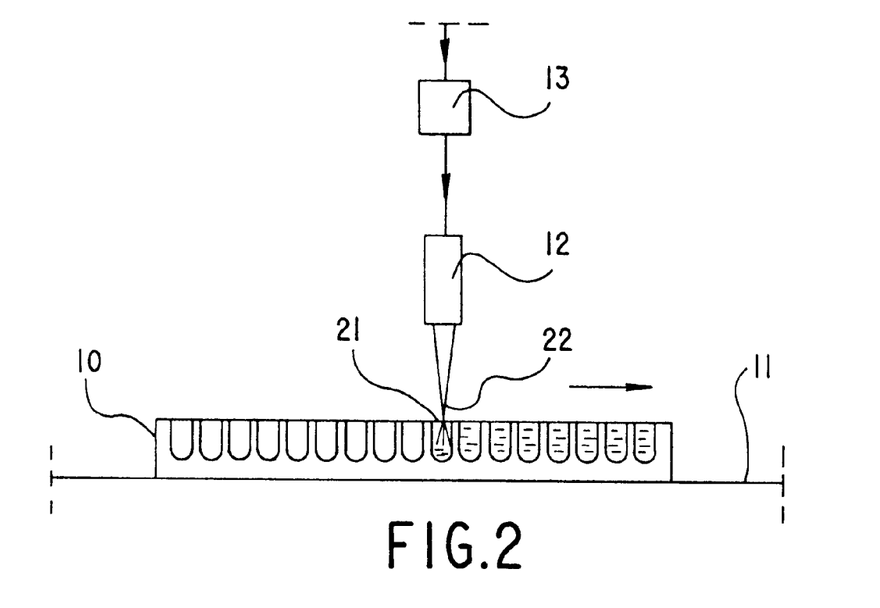
FIG. 2 shows a magnified detail of the dosing device, in which a sample plate and a dosing nozzle are seen from the side.

FIG. 2 shows the situation of dosing of liquid into the sample well of a sample plate. It can be seen from FIG. 2 that from the dosing nozzle 12 above the sample plate 10, liquid 22 is dosed into the sample well 21 of the sample plate 10 which liquid can be, for example, liquid meant for the coating of the sample well 21 or sample solution. The sample well 21 rinsing liquid can, however, also be dosed in the same way.

FIG. 2 illustrates with an arrow the fact that the sample plate 10 on the conveyor 11 is moving in relation to the dosing nozzle 12. In this embodiment, the movement of the sample plate 10 has been arranged to take place periodically, in such a way that the sample well 21 is always stopped at the dosing nozzle 12 for dosing. After the sample well 21 has been filled, the sample plate 10 is moved in such a way that the next sample well or row of sample wells moves to the dosing nozzle 12.

Figure 3:
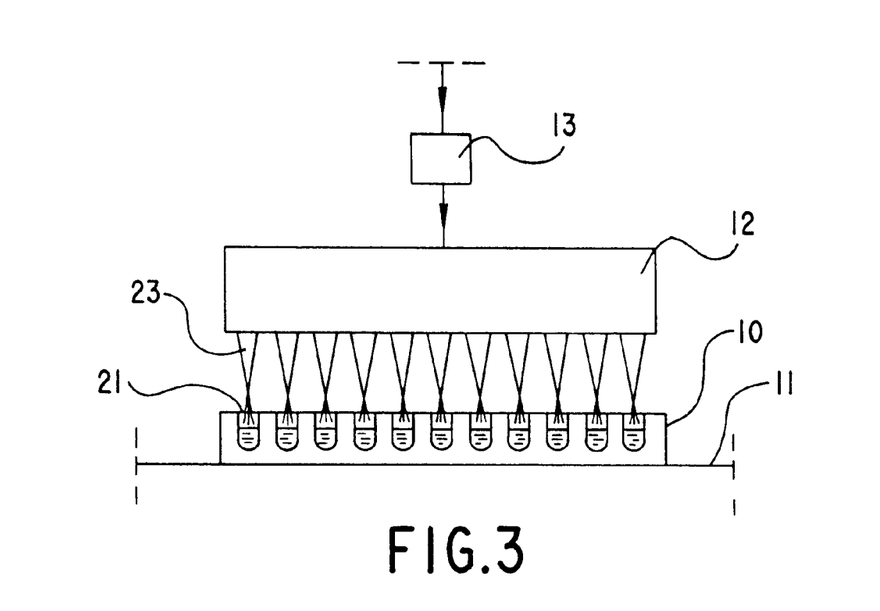
FIG. 3 shows a detail of the dosing device in FIG. 2, with a sample plate and a dosing nozzle seen from another direction.

FIG. 3 shows the dosing equipment in FIG. 2 seen from another direction. It can be seen from the figure that the dosing nozzle 12 of the sample plate 10 which is on the conveyor 11 comprises several nozzle tips 23, the number of which is the same as the number of the sample wells 21 in one row of the sample plate 10. In this way it is possible to dose into the entire row of sample wells at once when the sample plate has been stopped for dosing.

Figure 4:
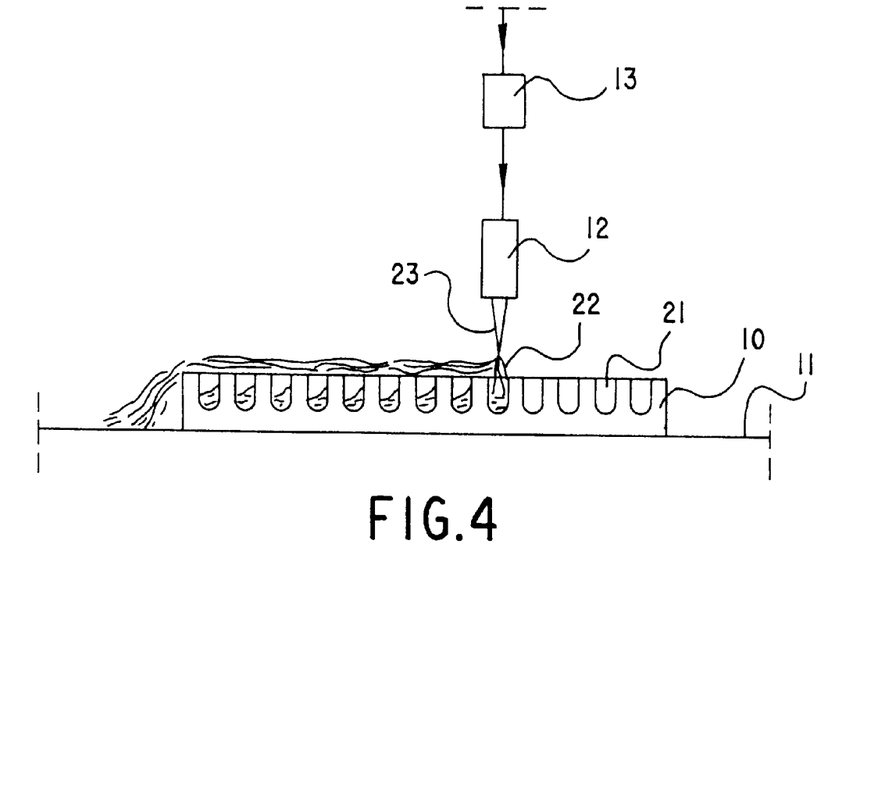
FIG. 4 corresponds to FIG. 2 and shows a sample plate and another embodiment of the dosing device's dosing nozzle.

FIG. 4 shows another embodiment of the sampling equipment in FIG. 2, in which the movement of the sample plate 10 is continuous. In such case the amount of liquid 22 coming from the dosing nozzle 12 has been adjusted to be such that a sample well 21 moves away from the nozzle 12 only after the amount of liquid dosed into the sample well 21 is sufficient. As the sample plate 10 proceeds at a uniform speed, each row of sample wells is dosed in turn. As in FIG. 3, the number of dosing tips 23 in the dosing nozzle 12 is also in this example equal to the number of sample wells adjacent to each other in one row of a sample plate.

It is natural that in the continuous dosing method described in FIG. 4 the dosing is not as accurate as in the periodical dosing method described in FIG. 2. It can be seen from FIG. 4 that dosing liquid inevitably also spills over the rims of the sample wells 21 of the sample plate 10. This is, however, of no significance, at least when dosing washing or rinsing liquid, for example.

Figure 5:
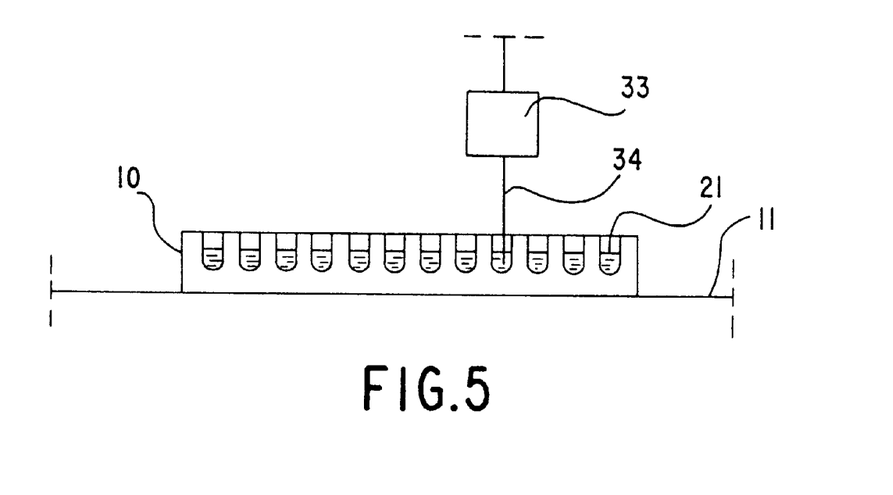
FIG. 5 corresponds to FIG. 2 and shows a sample plate and the vibrator device of the dosing device, seen from the side.

FIG. 5 shows another embodiment of the vibrator device used in conjunction with the dosing of the sample plate 10. The vibrator device comprises a vibrator element 33, which is, for example, an ultrasonic vibrator, to which one or more needles or spikes 34 have been attached. The needles 34 are dipped in the liquid dosed into the sample well 21 of the sample plate 10, after which the liquid in the well is made to vibrate using the vibrator device. In this way, air bubbles are removed from the dosed liquid and at the same time it is ensured that the dosed liquid is well in contact with the walls of the sample well 21. Thus either the shaker described in FIG. 1 or the ultrasonic vibrator described here, or both, can be used for this purpose.

Figure 6:
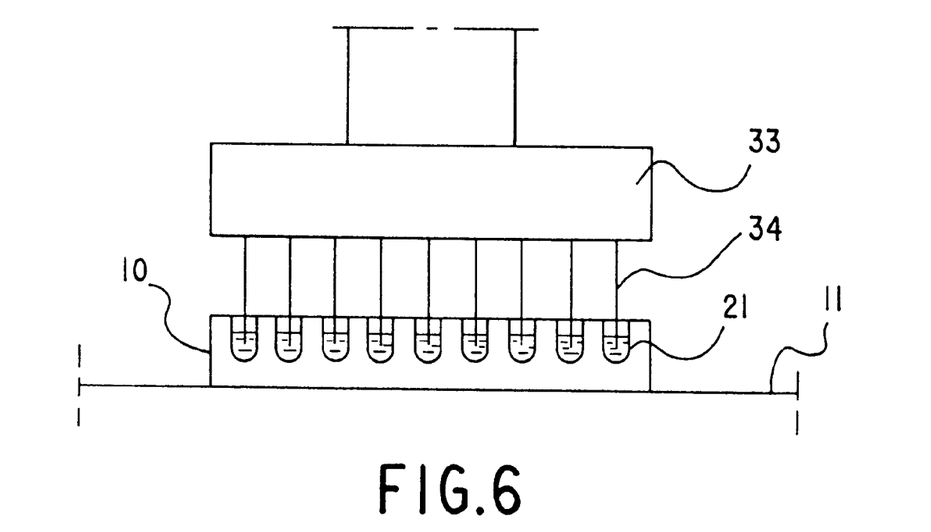
FIG. 6 shows the sample plate and the vibrator device of the dosing device shown in FIG. 5, seen from another direction.

As shown in FIG. 6, the needles 34 fixed to the vibrator element 33 can be placed in a row which has as many needles as there are sample wells 21 in a row in the sample plate 10. The arrangement then corresponds to the dosing nozzle 12 described in FIG. 3, which has as many nozzle tips as there are sample wells in a row in the sample plate. The difference is that the nozzle tips of the dosing nozzle are not dipped into the sample wells of the sample plate. The points of the row of needles 34 of the vibrator element 33 are, however, dipped into the liquids dosed into the sample wells 21 of the sample plate 10.

After the liquid has been dosed, the sample plate can be centrifuged. The purpose of centrifuging is to ensure that the liquid dosed will certainly go to the bottom of the sample well. At the same time, air bubbles are removed from the liquid. Thus the use of a centrifuge and various vibrators can be alternatives to each other, but also complementary to each other when used together.

Figure 7:
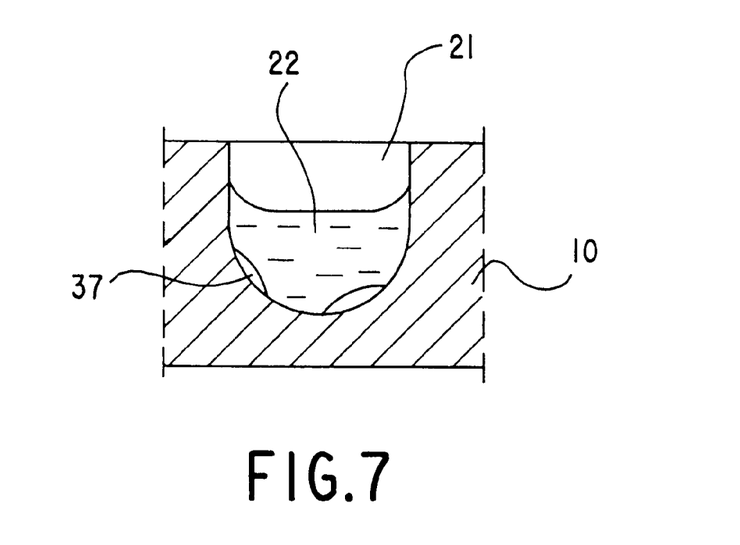
FIG. 7 shows a vertical section of the sample well of a sample plate after dosing of liquid.

FIG. 7 shows a vertical section of the sample well 21 of the sample plate 10, into which liquid 22 has been dosed. It can be seen from the figure that there remain air bubbles 37 between the liquid 22 and the wall of the sample well 21. Particularly when the sample plate 21 is small and its bottom part is angular in shape, the entire bottom part of the sample well may remain empty. It is clear that if the sample well 21 is filled incompletely like this, the walls of the sample well will not be properly coated. Likewise, if the sample well has to be washed or rinsed, rinsing and washing cannot be properly carried out when the well has air bubbles in it and is incompletely filled. According to the invention, incomplete filling of a sample well can be avoided and air bubbles removed by means of vibrators as described in FIGS. 1, 5 or 6, or by means of a centrifuge as described in FIG. 8.

Figure 8:
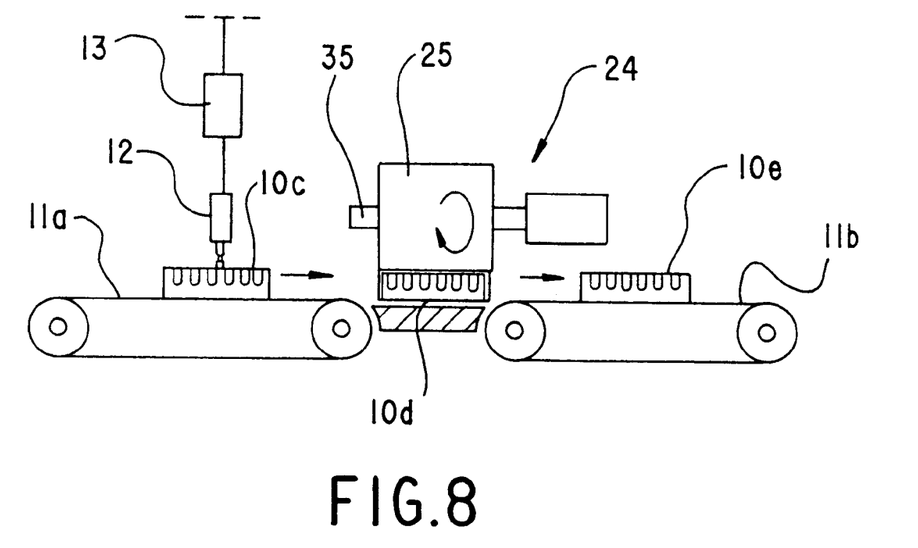
FIG. 8 shows a side view of a sample plate conveyor and the centrifuge used during the sample plate filling stage.
Figure 9:
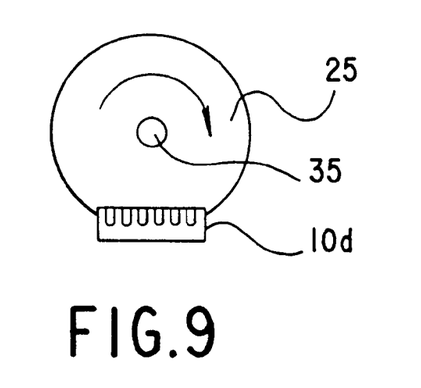
FIG. 9 shows the centrifuge drum shown in FIG. 8, seen from the direction of its axis.

FIG. 8 shows an equipment arrangement which incorporates a centrifuge 24. This equipment comprises a sample plate 10*c* on a conveyor 11, and another sample plate 10*d*, which has already been placed in the centrifuge 24 in such a way that the sample wells open towards the axis 35 of the drum 31 of the centrifuge 24. When the drum 31 rotates, the liquid in the sample wells of the sample plate 10 moves to the bottom of the sample well. In this way the liquid in the sample well is efficiently moved to the bottom of the sample plate and any air bubbles in the liquid are removed. FIG. 9 shows separately the rotatable drum 25 of the centrifuge 24 and the sample plate placed in it as described in FIG. 6.

As the sample will remain in the small sample wells of the sample plate due to the liquid's surface tension, even when the sample plate is turned upside down, various sample plates can be placed at different sides on the circumference of the drum 25 of the centrifuge 24. The sample wells of the sample plates 10 will not empty when they are placed in the drum, even if the sample plates 10 are upside down at times.

Figure 10:
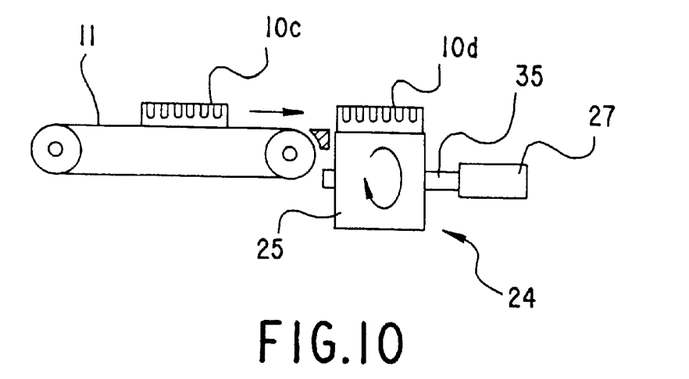
FIG. 10 shows a side view of the sample plate conveyor and the centrifuge used during the sample plate emptying stage.
Figure 11:
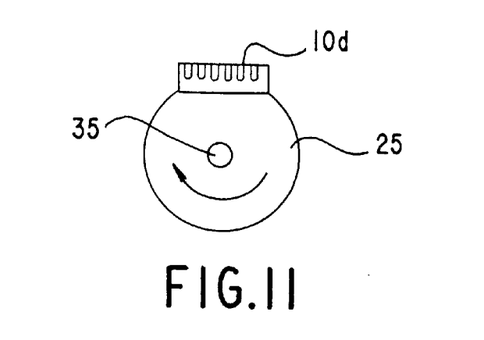
FIG. 11 shows the centrifuge drum shown in FIG. 10 seen from the direction of its axis.

Centrifuging can also be used for emptying a sample well. FIG. 10 shows equipment, or part of it, which has a centrifuge 24 used for emptying a sample well. In the equipment arrangement in FIG. 10 the conveyor 11 conveys the sample plate 10 to the emptying centrifuge 24. The centrifuge 24 comprises a drum 25, into the holders of which a sample plate 10 is placed in such a way that the sample wells open away from the axis 35 of the drum 25 of the centrifuge 24. The drum 25 is rotated by means of a rotating motor 27. In FIG. 11 is seen the drum 25 of the centrifuge in FIG. 10 as seen from the direction of the axis and a sample plate 10 fixed to the circumference of the drum.

As the sample will remain in the small sample wells of the sample plate due to the liquid's surface tension, even when the sample plate is turned upside down, various sample plates can be placed at different sides on the circumference of the drum 25 of the centrifuge 24. The sample wells of the sample plates 10 will not empty when they are placed on the circumference of the drum, even if the sample plates 10 are upside down at times. The sample wells are not emptied until centrifuging.

Figure 12:
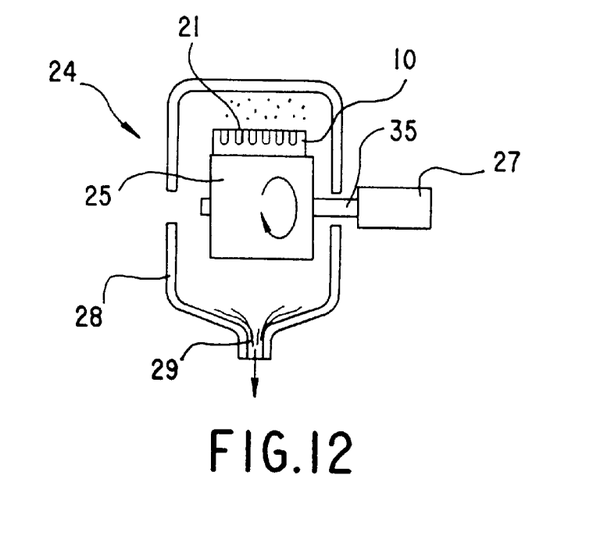
FIG. 12 shows a detail of the centrifuge shown in FIG. 10 during centrifuging, seen from the side.

FIG. 12 shows the situation of emptying by centrifuging, in which a sample plate 10 fixed to the circumference of the drum 25 of the centrifuge 24 is rotated by means of a rotating motor 27. In such case the liquid in the sample wells 21 of sample plate 10 is centrifuged and removed by the action of centrifugal force from the sample wells. A protective casing 28 has been formed in the centrifuge 24 for the liquid that is removed and an opening 29 in it, through which the liquid removed with the centrifuge can be collected. In this way, even small sample wells can be efficiently emptied, in which case washing and rinsing function in the intended way.

Figure 13:
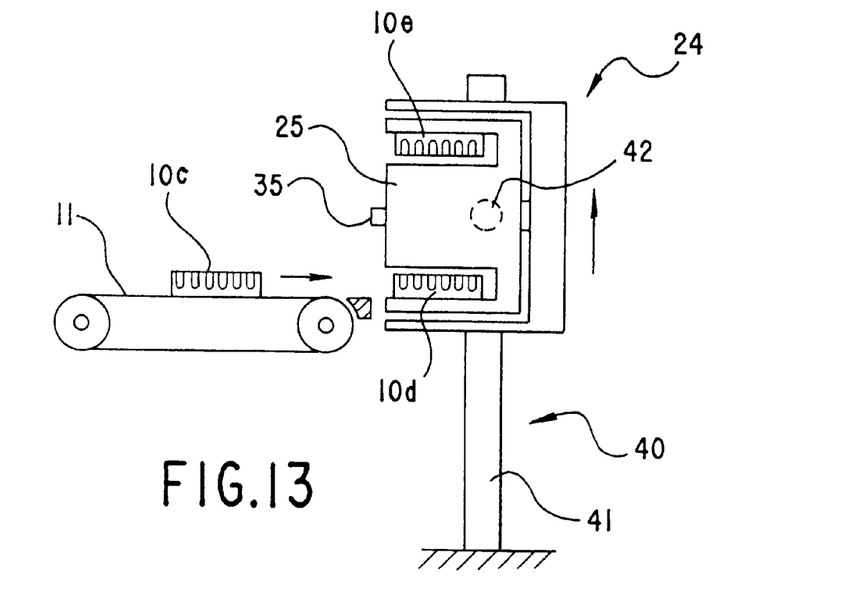
FIG. 13 shows the sample plate conveyor and another embodiment of the centrifuge, seen from the side.

In FIG. 13, there is a sample plate 10c conveyor 11 and another embodiment of the centrifuge 24, which has been fixed to a stand. The centrifuge 24 has been placed in the slide 41 of the stand 40 in such a way that it is possible to move the centrifuge 24 vertically. In FIG. 13, the centrifuge 24 is in the stand 40 in its upper position. In such case, the sample plates 10c to be fed into the centrifuge 24 come into the holders situated on the circumference of the drum 25 of the centrifuge 24 in such a way that the sample wells of the sample plates 10d and 10e open towards the inside of the drum 25, that is, towards the axis 35 of the drum 25. The sample wells of the sample plates 10d and 10e are so small that due to the liquid's surface tension the liquid in the sample wells is not removed although the sample wells are turned upside down.

Figure 14:
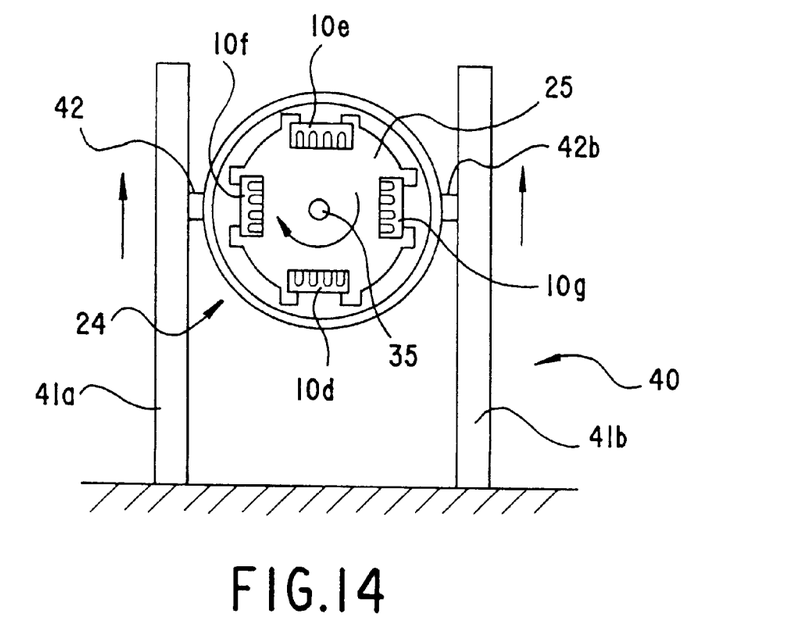
FIG. 14 shows the centrifuge in FIG. 13 from another direction, seen from the side.

In FIG. 14 is seen the centrifuge 24 in FIG. 13, seen from another direction. The centrifuge 24 is in the stand 40 in its upper position supported on the slides 41, and the axis 35 of the drum 25 is horizontal. The sample plates 10d–10g are on the circumference of the drum 25 in their holders with the sample wells directed towards the axis 35 of the drum 25. Thus directed, the sample plates 10d–10g are at the filling stage. The centrifuge 24 can now be started, in which case the liquid in the sample wells of the sample plates 10d–10g is centrifuged by the action of centrifugal force into the bottom of the sample wells and the air bubbles are removed from the sample wells.

Figure 15:
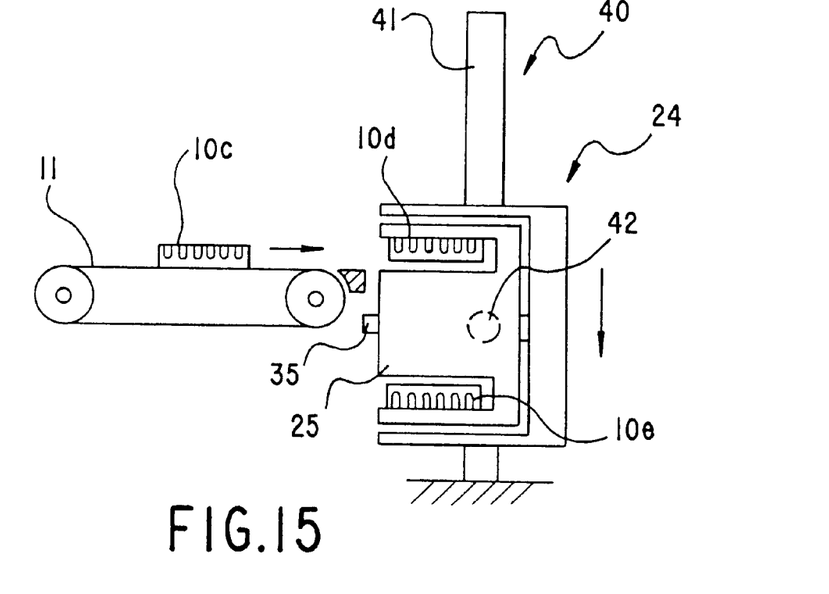
FIG. 15 corresponds to FIG. 13 and shows the centrifuge in another position.

In FIG. 15, the centrifuge 24 is in the stand 40 in its lower position. Now the sample plates 10c to be fed into the centrifuge 24 come into the holders situated on the circumference of the centrifuge 24 drum 25 in such a way that the sample wells of the sample plates 10d and 10e open outwards, that is away from the axis 35 of the drum 25.

Figure 16:
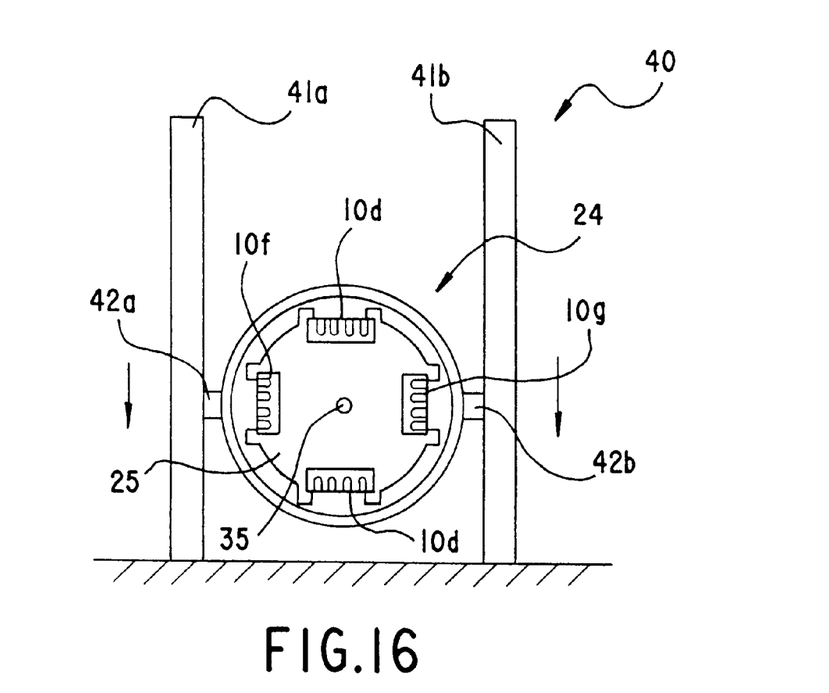
FIG. 16 corresponds to FIG. 14 and shows the centrifuge in another position.

FIG. 16 shows the centrifuge 24 from another direction. The centrifuge 24 is in the stand 40 in its lower position supported on the slides 41, and the axis 35 of the drum 25 is horizontal. Now the sample plates 10d–10g are not, however, centrifuged in this position, but the centrifuge 24 is turned 90° by means of axles 42a and 42b so that the axis 35 of the drum 25 is vertical.

Figure 17:
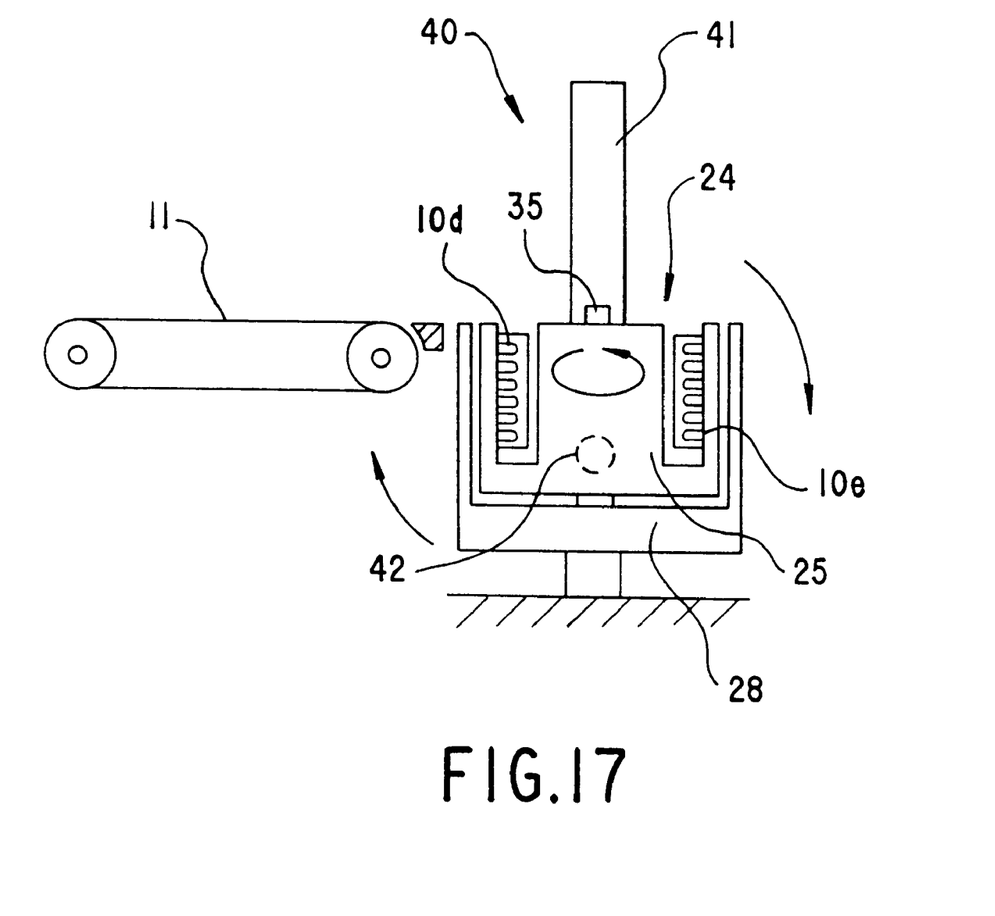
FIG. 17 corresponds to FIG. 15 and shows the centrifuge turned to the emptying position of the sample wells.

In FIG. 17, the centrifuge 24 is in the sample well emptying position, in which the centrifuge 24 has been turned around the axle 42 in such a way that the axis 35 of the drum 25 is vertical. When the centrifuge 24 is now started, the sample wells of the sample plates 10d–10g, which are directed away from the axis 35 of the drum 25, are emptied by the action of centrifugal force and the liquid in the sample wells is centrifuged to the walls of the protective casing 28 of the centrifuge 24 and from there further to the bottom of the centrifuge. This embodiment is advantageous because the liquid that is being removed from the sample wells will not fall from the walls of the protective casing 28 back onto the sample plates when centrifuged. The liquid is removed from the bottom of the protective casing 28 in the way described in FIG. 12, for example.

It is therefore possible to carry out both the centrifuging required for filling the sample wells of the sample plates and the centrifuging required for emptying the sample wells using the device shown in FIGS. 13 to 17.

It is obvious to a person skilled in the art that the different embodiments of the invention may vary within the scope of the claims presented below.

What is claimed is:

1. A method for handling a sample plate (10) having a plurality of sample wells (21), comprising the steps of dosing liquid (22) into the sample wells (21) of the sample plate (10); centrifuging the sample plate (10) to take the dosed liquid (22) to the bottom of the sample wells (21) and to remove air bubbles from the sample wells (21); and thereafter centrifuging the sample plate (10) to remove the dosed liquid (22) from the sample wells (21).

2. A method as claimed in claim 1, wherein in order to take the dosed liquid (22) to the bottom of the sample wells (21), the sample plate (10) is centrifuged in a centrifuge (24) with the axis of the centrifuge (24) either horizontal or vertical, and in order to remove the dosed liquid from the sample wells, the sample plate is certifuged in the centrifuge (24) with the axis of the centrifuge (24) turned to a vertical position.

3. A method as claimed in claim 1, wherein in order to fill the sample wells (21), the sample plate (10) is placed in the centrifuge (24) so that the sample wells are directed towards the axis of rotation (35) of a centrifuge drum (25) of the centrifuge (24), and the sample plate is centrifuged in order to throw the dosed liquid (22), by means of centrifugal force, against the bottom and walls of the sample wells, and that in order to empty the sample wells (21), the sample plate (10) is placed in the centrifuge (24) so that the sample wells (21) are directed away from the axis of rotation (35) of the centrifuge drum (25), and the sample plate is centrifuged in order to remove the dosed liquid (22), by means of centrifugal force, from the sample wells.

4. A method as claimed in claim 1, wherein the liquid (22) to be dosed is chosen from two or more liquid containers (15), and the liquid to be dosed is passed to the sample wells of the sample plate through a distributing valve (14) and via a dosing nozzle (12).

5. A method as claimed in claim 1, wherein compressed air or pressurised gas is fed into two or more liquid containers (15), and the liquid to be dosed is passed from one of said pressurised liquid containers through a distributing valve (14) and via a dosing nozzle (12) to the sample wells (21) of the sample plate (10).

6. A method as claimed in claim 1, wherein dosing of the liquid (22) into the sample wells (21) of the sample plate (10) is carried out periodically by moving the sample plate by means of a conveyor (11) and stopping the conveyor for dosing when the sample well is at a dosing nozzle (12).

7. A method as claimed in claim 1, wherein the dosing of the liquid (22) into the sample wells (21) of the sample plate (10) is carried out continuously by moving the sample plate by means of a conveyor (11) under a dosing nozzle (12) during dosing.

8. A method as claimed in claim 1, wherein the sample plate (10) or the liquid (22) in the sample wells (21) of the sample plate is vibrated to remove air bubbles or to bring the dosed liquid into contact with the bottom and walls of the sample wells.

9. A device for handling a sample plate (10) having a plurality of sample wells (21), which device comprises a dosing device for feeding liquid (22) into the sample wells (21) of the sample plate and a device for removing liquid from the sample wells, wherein the sample plate (10) handling device comprises a centrifuge (24) for centrifuging the sample plate, a feeding device (11) for feeding the sample plate into the centrifuge, sample plate fixing elements for fixing the sample plate to a centrifuge drum (25) of the centrifuge (24) to direct the sample wells (21) of the sample plate towards the axis of rotation (35) of the centrifuge drum, and sample plate fixing elements for fixing the sample plate to the centrifuge drum to direct the sample wells of the sample plate away from the axis of rotation of the centrifuge drum.

10. A device as claimed in claim 9, wherein the centrifuge (24) comprises a turning element (42) by means of which the centrifuge can be turned so that the axis (35) of the centrifuge drum (25) is vertical during centrifuging.

11. A device as claim in claim 9, wherein the dosing device comprises two or more liquid containers (15) from which liquid (22) to be dosed can be dosed through a distributing valve (14) and via a dosing nozzle (12) into the sample wells (21) of the sample plate (10).

12. A device as claimed in claim 9, wherein the dosing device comprises a compressed air or compressed gas device connected to two or more liquid containers (15) for feeding compressed air or gas into these containers, and a distributing valve (14) and a dosing nozzle (12), by means of which the liquid to be dosed can be chosen from one of said containers for dosing into the sample wells (21) of the sample plate (10).

13. A device as claim in claim 9, wherein the dosing device comprises a vibrator (32, 33) for vibrating the liquid (22) in the sample wells (21) of the sample plate (10).

14. A device as claimed in claim 13, wherein the vibrator device (32) is located in conjunction with a sample plate (10) conveyor belt (11).

15. A device as claimed in claim 13, wherein the vibrator device (33) comprises at least one spike or needle (34), which can be positioned in the liquid (22) in the sample well (21) of the sample plate (10) in order to vibrate the liquid.

* * * * *